(12) United States Patent
Foxman

(10) Patent No.: US 12,110,564 B2
(45) Date of Patent: Oct. 8, 2024

(54) TEST TO DISTINGUISH VIRAL-ONLY FROM BACTERIAL INFECTION OR VIRAL/BACTERIAL COINFECTION USING A RESPIRATORY SWAB

(71) Applicant: YALE UNIVERSITY, New Haven, CT (US)

(72) Inventor: Ellen Foxman, West Hartford, CT (US)

(73) Assignee: Yale University, New Haven, CT (US)

( * ) Notice: Subject to any disclaimer, the term of this patent is extended or adjusted under 35 U.S.C. 154(b) by 876 days.

(21) Appl. No.: 17/052,882

(22) PCT Filed: May 6, 2019

(86) PCT No.: PCT/US2019/030877
§ 371 (c)(1),
(2) Date: Nov. 4, 2020

(87) PCT Pub. No.: WO2019/217296
PCT Pub. Date: Nov. 14, 2019

(65) Prior Publication Data
US 2021/0363601 A1    Nov. 25, 2021

Related U.S. Application Data

(60) Provisional application No. 62/667,697, filed on May 7, 2018.

(51) Int. Cl.
*C12Q 1/70*     (2006.01)
*C12Q 1/689*   (2018.01)
*G01N 33/569*  (2006.01)

(52) U.S. Cl.
CPC ............... *C12Q 1/70* (2013.01); *C12Q 1/689* (2013.01); *G01N 33/56911* (2013.01); *G01N 33/56983* (2013.01)

(58) Field of Classification Search
CPC .... C12Q 1/70; C12Q 1/689; C12Q 2600/158; C12Q 1/701; G01N 33/56911; G01N 33/56983; G01N 2800/12
See application file for complete search history.

(56) References Cited

U.S. PATENT DOCUMENTS

2005/0163862 A1   7/2005   Forceville et al.
2014/0128286 A1   5/2014   Khabar et al.
2016/0084762 A1   3/2016   Goix et al.

FOREIGN PATENT DOCUMENTS

WO   2009024834 A2   2/2009
WO   2012169887 A2   12/2012
(Continued)

OTHER PUBLICATIONS

Redwine et al., The human cytoplasmic dynein interactome reveals novel activators of motility, eLife, 2017, e28257, pp. 1-27 (Year: 2017).*

(Continued)

*Primary Examiner* — Savitha M Rao
*Assistant Examiner* — Andrew P Lee
(74) *Attorney, Agent, or Firm* — Saul Ewing LLP; Justin Crotty; Kathryn Doyle

(57) ABSTRACT

In one aspect the invention provides a method for distinguishing between a viral-only infection of the upper respiratory tract or a bacterial or viral/bacterial coinfection in a patient by analyzing a respiratory sample.

20 Claims, 3 Drawing Sheets

(56) References Cited

FOREIGN PATENT DOCUMENTS

| WO | 2017004390 A1 | 1/2017 |
|---|---|---|
| WO | 2017149547 A1 | 9/2017 |
| WO | 2017149548 A1 | 9/2017 |
| WO | 2017214061 A1 | 12/2017 |
| WO | 2018071498 A1 | 4/2018 |

OTHER PUBLICATIONS

Arvia, et al., "Detection of 12 respiratory viruses by duplex real time PCR assays in respiratory samples", Mol Cell Probes. 29(6), Dec. 2015, 408-413.

Chen, Yin, et al., "Rhinovirus Induces Airway Epithelial Gene Expression through Double-Stranded RNA and IFN- Dependent Pathways", American Journal of Respiratory Cell and Molecular Biology 34(2), 1Oct. 6, 2005, 192-203.

Ioannidis, et al., "Plasticity and Virus Specificity of the Airway Epithelial Cell Immune Response During Respiratory Virus Infection", J Virol. 86 (10), May 2012, 5422-5436.

Landry, Marie L., et al., "Antiviral Response in the Nasopharynx Identifies Patients With Respiratory Virus Infection", The Journal of Infectious Diseases 17(6), Mar. 15, 2018, 897-905.

Scagnolari, Carolina, et al., "Evaluation of viral load in infants hospitalized with bronchiolitis caused by respiratory syncytial virus", Medical Microbiology and Immunology 201(3), Mar. 10, 2021, 311-317.

Selvaggi, et al., "Interferon Lambda 1-3 Expression in Infants Hospitalized for RSV or HRV Associated Bronchiolitis", J Infect. 68(5), Jan. 2, 2014, 467-477.

Wagener, Ariane H., et al., "dsRNA-induced changes in gene expression profiles of primary nasal and bronchial epithelial cells from patients with asthma, rhinitis and controls", Respiratory Research 15(1)9, Jan. 2014, 1-9.

International Search Report and Written Opinion issued by the International Searching Authority on Feb. 20, 2018 for International Patent Application No. PCT/US2017/056076, 16 pages.

* cited by examiner

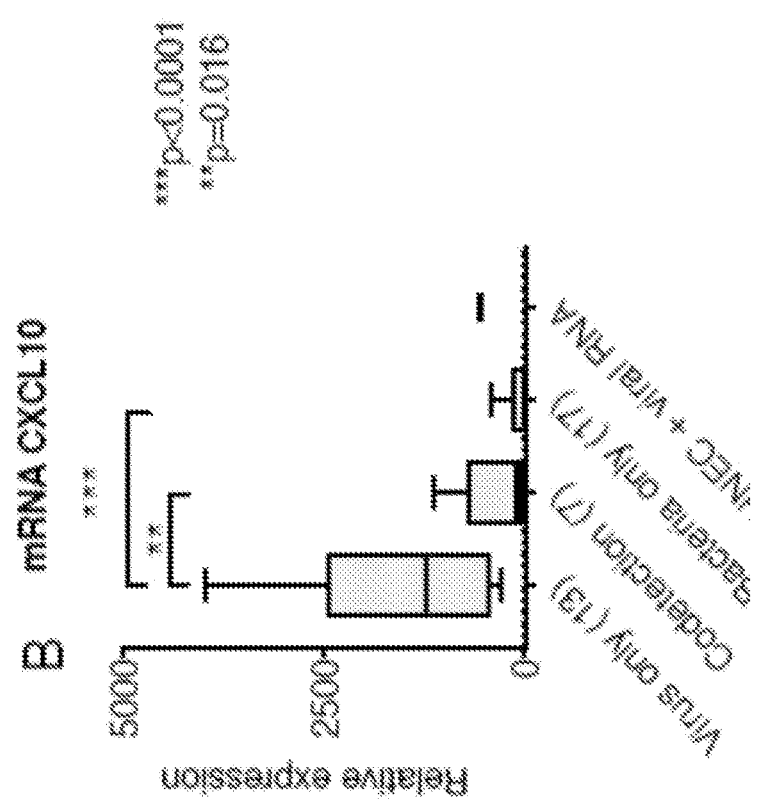
FIG. 2A
FIG. 2B
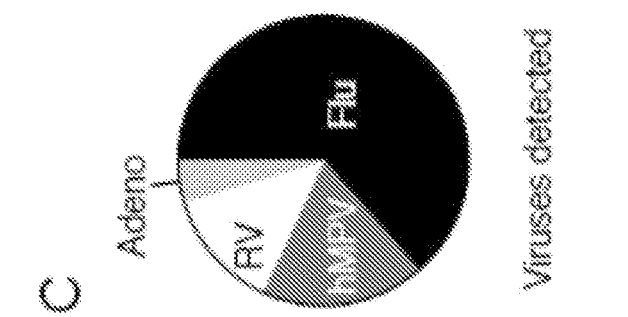
FIG. 2C

TEST TO DISTINGUISH VIRAL-ONLY FROM BACTERIAL INFECTION OR VIRAL/BACTERIAL COINFECTION USING A RESPIRATORY SWAB

CROSS-REFERENCE TO RELATED APPLICATIONS

The present application is a 35 U.S.C. § 371 national phase application from, and claiming priority to, International Application No. PCT/US2019/030877, filed May 6, 2019, which claims priority under 35 U.S.C. § 119(e) to U.S. Provisional Patent Application No. 62/667,697 filed May 7, 2018, which are hereby incorporated by reference in their entireties herein.

STATEMENT REGARDING FEDERALLY SPONSORED RESEARCH OR DEVELOPMENT

This invention was made with government support under AI119137 awarded by National Institutes of Health. The government has certain rights in the invention.

BACKGROUND OF THE INVENTION

Antibiotic overuse drives the emergence of antibiotic resistant bacteria, an increasingly urgent threat to global public health. Outpatient visits for acute respiratory illnesses generate more inappropriate antibiotic prescriptions than visits for any other conditions: a recent report showed that half of the ~70 million annual prescriptions for acute respiratory conditions are not warranted. Among these, pharyngitis is one of the illnesses most highly associated with antibiotic overuse (72% of prescriptions for adults and 35% for children not indicated). Viruses are responsible for 70-90% of symptomatic acute upper respiratory infections. However, in general, antibiotics are only indicated for illnesses caused by bacteria or viral/bacterial coinfection, since antibiotics kill bacteria but not viruses. While there are some diagnostic tests available to rule in infection with specific respiratory pathogens (e.g. influenza virus, RSV, Group A streptococcal bacterial infection), there is no simple test to distinguish viral-only illnesses from illnesses involving bacteria. If such a test were available, the information would be expected to predict whether antibiotics would be of benefit to the patient, and would help inform decision-making about antibiotic use.

Therefore there is a need in the art for a practical and reliable test to distinguish between viral-only respiratory tract infection and infections involving bacteria. The present invention addresses this need.

SUMMARY OF THE INVENTION

In one aspect the invention provides a method for detecting a viral-only or a bacterial-associated respiratory infection in a patient, the method comprising:
a. analyzing a respiratory sample to determine a level of at least one respiratory virus infection-associated molecule and/or a level of at least one bacterial respiratory infection-associated molecule and a level of a housekeeping gene by measuring mRNA;
b. normalizing the level of the at least one respiratory virus infection-associated molecule and/or the level of the at least one bacterial respiratory infection-associated molecule to the level of the housekeeping gene to determine a normalized level of the at least one respiratory virus infection-associated molecule and/or a normalized level of the at least one bacterial respiratory infection-associated molecule;
c. comparing the normalized level of the at least one respiratory virus infection-associated molecule and/or the normalized level of the at least one bacterial respiratory infection-associated molecule with a predetermined reference level for the at least one respiratory virus infection-associated molecule and/or a predetermined reference level of the at least one bacterial respiratory infection-associated molecule; and,
wherein if the normalized level of the at least one respiratory virus infection-associated molecule is above the respective reference level, the patient is determined to have a respiratory viral infection;
if the normalized level of the at least one bacterial respiratory infection-associated molecule is above the respective reference level, the patient is determined to have a bacterial-associated respiratory infection.

In various embodiments, the mRNA is measured by reverse transcription-qPCR.

In various embodiments, the at least one respiratory virus infection-associated molecule is selected from the group consisting of FAM160A1, CXCL9, CXCL11, IDO1, IRG1, TFEC, EPHA4, DGCR2, DGCR11, SAA2; SAA2-SAA4; SAA4, OR8B4, STAT2, ATP13A3, CXCL10, PLA2G7, DRAM1, ZNF407, MS4A7, ADGRD1, OR6C2, PTTG11P, NFAT5, GSN, EDA, ROBO2, PRNP, THRAP3, CCDC184, SEMA6D, SOCS6, ITPKC, DGKD, SRPRB, RNF148, TRIM67, CTH, ZMYND11, PNLIPRP3, MAP4, GAD2, KIDINS220, ST5, MCM3AP, LIPG, WBP5, ITPKA, WDR78, PNPT1, FAM184B, P2RX7, VAMP4, ARVCF, TEX9, OR52N4, TAAR2, CP, NIPSNAP3A, NIPSNAP3B, OSTM1, TRIM69, MDM1, SLC32A1, ERN2, LINC01521, AK4, EXOSC6, CHFR, FBXO43, HUS1B, PLCB1, CECR6 and DSG2.

In various embodiments, the at least one respiratory virus infection-associated molecule is CXCL10.

In various embodiments, the at least one bacterial respiratory infection-associated molecule is selected from the group consisting of SEP15, SLC25A40, ANKRD13A, H2AFZ, TLK1, ARPC2, BSG, MSRB1, PI3, SCAF8, TIAM2, ZMAT2, CAP1, ARPC3, LAMTOR5, ACAA1, RAP1A, SSR2, ZDHHC3, ZNF680, RHOG, PRKACB, SHOC2, CCDC126, FAM102A, TAF10, LSM1, NECAP1, PHB, SNX3, FAM122B, SEC63, U2AF1, ZC3H14, ARHGDIB, ATE1, PSMB7, FLI1, CRTC2, GHITM, UBE2D2, NFU1, IDH3A, ZNF791, PROK2, MLF2, MXI1, EIF4B, NUMA1, PCBD1, BAG6, STX7, CREB1, COPS3, C1orf43, FDFT1, VKORC1, ACTR10, CCND3, GOLGA7, TMEM167A, RPS8, SNORD55, SNORD46, SNORD38A, SNORD38B, ABTB1, HSD17B11, CAMK2G, ATG4C, PHF3, QRICH1, MTHFS, CDKSRAP2, UBE2W, DPY19L1, HIPK1, TXNIP, IRAK4, APOPT1, PROK2 and TRMT112.

In various embodiments, the at least one bacterial respiratory infection-associated molecule is SEP15.

In various embodiments, the housekeeping gene comprises β-actin, HPRT, or GAPDH.

In another aspect, the invention provides a method for detecting a viral-only or a bacterial-associated respiratory infection in a patient, the method comprising:
a. analyzing a respiratory sample to determine a level of at least one respiratory virus infection-associated molecule and/or a level of at least one bacterial respiratory infection-associated molecule by measuring protein;

b. comparing the level of the at least one respiratory virus infection-associated molecule and/or the level of the at least one bacterial respiratory infection-associated molecule with a predetermined reference level for the at least one respiratory virus infection-associated molecule and/or a predetermined reference level of the at least one bacterial respiratory infection-associated molecule; and,
   wherein if the level of the at least one respiratory virus infection-associated molecule is above the respective reference level, the patient is determined to have a respiratory viral infection;
   if the level of the at least one bacterial respiratory infection-associated molecule is above the respective reference level, the patient is determined to have a bacterial-associated respiratory infection.

In various embodiments, the level of the at least one respiratory virus infection-associated molecule and/or the level of the at least one bacterial respiratory infection-associated molecule is measured by immunoassay.

In various embodiments, the at least one respiratory virus infection-associated molecule is selected from the group consisting of FAM160A1, CXCL9, IDO1, IRG1, TFEC, EPHA4, DGCR2, DGCR11, SAA2; SAA2-SAA4; SAA4, OR8B4, STAT2, ATP13A3, CXCL10, PLA2G7, DRAM1, ZNF407, MS4A7, ADGRD1, OR6C2, PTTG11P, NFAT5, GSN, EDA, ROBO2, PRNP, THRAP3, CCDC184, SEMA6D, SOCS6, ITPKC, DGKD, SRPRB, RNF148, TRIM67, CTH, ZMYND11, PNLIPRP3, MAP4, GAD2, KIDINS220, ST5, MCM3AP, LIPG, WBP5, ITPKA, WDR78, PNPT1, FAM184B, P2RX7, VAMP4, ARVCF, TEX9, OR52N4, TAAR2, CP, NIPSNAP3A, NIPSNAP3B, OSTM1, TRIM69, MDM1, SLC32A1, ERN2, LINC01521, AK4, EXOSC6, CHFR, FBXO43, HUS1B, PLCB1, CECR6 and DSG2.

In various embodiments, the at least one respiratory virus infection-associated molecule is CXCL10.

In various embodiments, the at least one bacterial respiratory infection-associated molecule is selected from the group consisting of SEP15, SLC25A40, ANKRD13A, H2AFZ, TLK1, ARPC2, BSG, MSRB1, PI3, SCAF8, TIAM2, ZMAT2, CAP1, ARPC3, LAMTOR5, ACAA1, RAP1A, SSR2, ZDHHC3, ZNF680, RHOG, PRKACB, SHOC2, CCDC126, FAM102A, TAF10, LSM1, NECAP1, PHB, SNX3, FAM122B, SEC63, U2AF1, ZC3H14, ARHGDIB, ATE1, PSMB7, FLI1, CRTC2, GHITM, UBE2D2, NFU1, IDH3A, ZNF791, PROK2, MLF2, MXI1, EIF4B, NUMA1, PCBD1, BAG6, STX7, CREB1, COPS3, C1orf43, FDFT1, VKORC1, ACTR10, CCND3, GOLGA7, TMEM167A, RPS8, SNORD55, SNORD46, SNORD38A, SNORD38B, ABTB1, HSD17B11, CAMK2G, ATG4C, PHF3, QRICH1, MTHFS, CDK5RAP2, UBE2W, DPY19L1, HIPK1, TXNIP, IRAK4, APOPT1, PROK2 and TRMT112.

In various embodiments, the at least one bacterial respiratory infection-associated molecule is SEP15.

In various embodiments, the levels of at least two nasal virus-associated molecules and/or at least two bacterial respiratory infection-associated molecules are determined and compared to the respective reference.

In various embodiments, the levels of at least three nasal virus-associated molecules and/or at least three bacterial respiratory infection-associated molecules are determined and compared to the respective reference levels.

In another aspect, the invention provides a method of treating a patient exhibiting symptoms of a respiratory infection, the method comprising:

a. analyzing a respiratory sample to determine a level of at least one respiratory virus infection-associated molecule and/or a level of at least one bacterial respiratory infection-associated molecule and a level of a housekeeping gene by measuring mRNA;
b. normalizing the level of the at least one respiratory virus infection-associated molecule and/or the level of the at least one bacterial respiratory infection-associated molecule to the level of the housekeeping gene to determine a normalized level of the at least one respiratory virus infection-associated molecule and/or a normalized level of the at least one bacterial respiratory infection-associated molecule;
c. comparing the normalized level of the at least one respiratory virus infection-associated molecule and/or the normalized level of the at least one bacterial respiratory infection-associated molecule with a predetermined reference level for the at least one respiratory virus infection-associated molecule and/or a predetermined reference level of the at least one bacterial respiratory infection-associated molecule; and,
   wherein if the normalized level of the at least one respiratory virus infection-associated molecule is above the respective reference level, the patient is treated for a respiratory viral infection;
   if the normalized level of the at least one bacterial-associated molecule is above the respective reference level, the patient is treated for a bacterial respiratory infection.

In another aspect, the invention provides a method of treating a patient exhibiting symptoms of a respiratory infection, the method comprising:

a. analyzing a respiratory sample to determine a level of at least one respiratory virus infection-associated molecule and/or a level of at least one bacterial respiratory infection-associated molecule by measuring protein;
b. comparing the level of the at least one respiratory virus infection-associated molecule and/or the level of the at least one bacterial respiratory infection-associated molecule with a predetermined reference level for the at least one respiratory virus infection-associated molecule and/or a predetermined reference level of the at least one bacterial respiratory infection-associated molecule; and,
   wherein if the normalized level of the at least one respiratory virus infection-associated molecule is above the respective reference level, the patient is treated for a respiratory viral infection;
   if the normalized level of the at least one bacterial-associated molecule is above the respective reference level, the patient is treated for a bacterial respiratory infection.

In another aspect, the invention provides a method of determining whether a subject who tests positive for the presence of bacterial or viral respiratory pathogen is a carrier or if the pathogen is part of the disease process, the method comprising:

a. analyzing a respiratory sample to determine a level of at least one respiratory virus infection-associated molecule, a level of at least one bacterial respiratory infection-associated molecule and a level of a housekeeping gene by measuring mRNA;
b. normalizing the level of the at least one respiratory virus infection-associated molecule and the level of the at least one bacterial respiratory infection-associated molecule to the level of the housekeeping gene to determine a normalized level of the at least one respiratory virus infection-associated molecule and a normalized level of the at least one bacterial respiratory infection-associated molecule;
c. comparing the normalized level of the at least one respiratory virus infection-associated molecule and the normalized level of the at least one bacterial respiratory infection-associated molecule with a predetermined reference level for the at least one respiratory virus infection-associated molecule and a predetermined reference level of the at least one bacterial respiratory infection-associated molecule; and,
wherein if the normalized level of the at least one respiratory virus infection-associated molecule is above the respective reference level, the patient is determined to have a respiratory viral infection;
if the normalized level of the at least one bacterial respiratory infection-associated molecule is above the respective reference level, the patient is determined to have a bacterial-associated respiratory infection;
if the normalized level of the at least one respiratory virus infection-associated molecule is above the respective reference level and the level of the at least one bacterial respiratory infection-associated molecule is above the respective reference level, the patient is determined to have both a respiratory viral infection and a bacterial respiratory infection;
if neither the level of the at least one respiratory virus infection-associated molecule nor the level of the at least one bacterial respiratory infection-associated molecule is above the respective reference level, the subject is determined to be a carrier.

In another aspect, the invention provides a method of determining whether a subject who tests positive for the presence of bacterial or viral respiratory pathogen is a carrier or if the pathogen is part of the disease process, the method comprising:
a. analyzing a respiratory sample to determine a level of at least one respiratory virus infection-associated molecule and/or a level of at least one bacterial respiratory infection-associated molecule by measuring protein;
b. comparing the level of the at least one respiratory virus infection-associated molecule and/or the level of the at least one bacterial respiratory infection-associated molecule with a predetermined reference level for the at least one respiratory virus infection-associated molecule and/or a predetermined reference level of the at least one bacterial respiratory infection-associated molecule; and,
wherein if the level of the at least one respiratory virus infection-associated molecule is above the respective reference level, the patient is determined to have a respiratory viral infection;
if the level of the at least one bacterial respiratory infection-associated molecule is above the respective reference level, the patient is determined to have a bacterial respiratory infection;
if the level of the at least one respiratory virus infection-associated molecule is above the respective reference level and the level of the at least one bacterial respiratory infection-associated molecule is above the respective reference level, the patient is determined to have both a respiratory viral infection and a bacterial respiratory infection;
if neither the level of the at least one respiratory virus infection-associated molecule nor the level of the at least one bacterial respiratory infection-associated molecule is above the respective reference level, the subject is determined to be a carrier.

In another aspect, the invention provides a method of detecting a bacterial-associated respiratory infection in a subject, the method comprising:
a. analyzing a respiratory sample to determine a level of at least one bacterial respiratory infection-associated molecule and a level of a housekeeping gene by measuring mRNA;
b. normalizing the level of the at least one bacterial respiratory infection-associated molecule to the level of the housekeeping gene to determine a normalized level of the at least one bacterial respiratory infection-associated molecule;
c. comparing the normalized level of the at least one bacterial respiratory infection-associated molecule with a predetermined reference level of the at least one bacterial respiratory infection-associated molecule; and,
wherein if the normalized level of the at least one bacterial respiratory infection-associated molecule is above the respective reference level, the patient is determined to have a bacterial-associated respiratory infection.

In another aspect, the invention provides a method of detecting a bacterial-associated respiratory infection in a subject, the method comprising:
a. analyzing a respiratory sample to determine a level of at least one respiratory virus infection-associated molecule and/or a level of at least one bacterial respiratory infection-associated molecule by measuring protein;
b. comparing the level of the at least one bacterial respiratory infection-associated molecule with a predetermined reference level for the at least one bacterial respiratory infection-associated molecule;
wherein if the level of the at least one bacterial respiratory infection-associated molecule is above the respective reference level, the patient is determined to have a bacterial respiratory infection.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 2A-2C depict RT-qPCR validation of viral-only biomarker CXCL10. CXCL10 mRNA level assessed by RT-qPCR from patient samples. FIGS. 2A and 2B depict plots that show CXCL10 mRNA level normalized to the level of housekeeping gene BActin mRNA in each sample. Values are expressed compared to the CXCL10 mRNA in resting unstimulated nasal epithelial cells. Horizontal bar shows level of CXCL10 mRNA found in primary human nasal epithelial cells stimulated in vitro with the viral RNA mimetic chemical SLR14 compared to the level in unstimulated cells. This finding is consistent with CXCL10 induction in viral pharyngitis. Asterisks represent significant p values (p=0.016; *p<0.0001). FIG. 2C depicts a pie chart that shows types of respiratory viruses detected in virus-only and coinfection patients in this sample set.

FIG. 3A depicts SEP15 mRNA level assessed by RT-qPCR from patient samples. Plot shows SEP15 mRNA level normalized to the level of housekeeping gene BActin mRNA in each sample. FIG. 3B depicts regulation of SEP15 in airway cells by reactive oxygen species. Primary airway epithelial cells were exposed to hydrogen peroxide or medium only for 30 minutes at 37° C., then stimulus was removed and cells were allowed to recover for 18 hr, at which time RNA was collected for RT-qPCR. Streptococcal bacterial infection is associated with reactive oxygen species production. This graph shows that exposure to reactive oxygen species induces SEP15 in primary airway epithelial cells in vitro, providing a biological explanation for its induction in bacterial pharyngitis but not viral pharyngitis. Other transcripts associated with this stress response were also enriched in the bacterial infection signature.

DETAILED DESCRIPTION

Definitions

Figure 1:
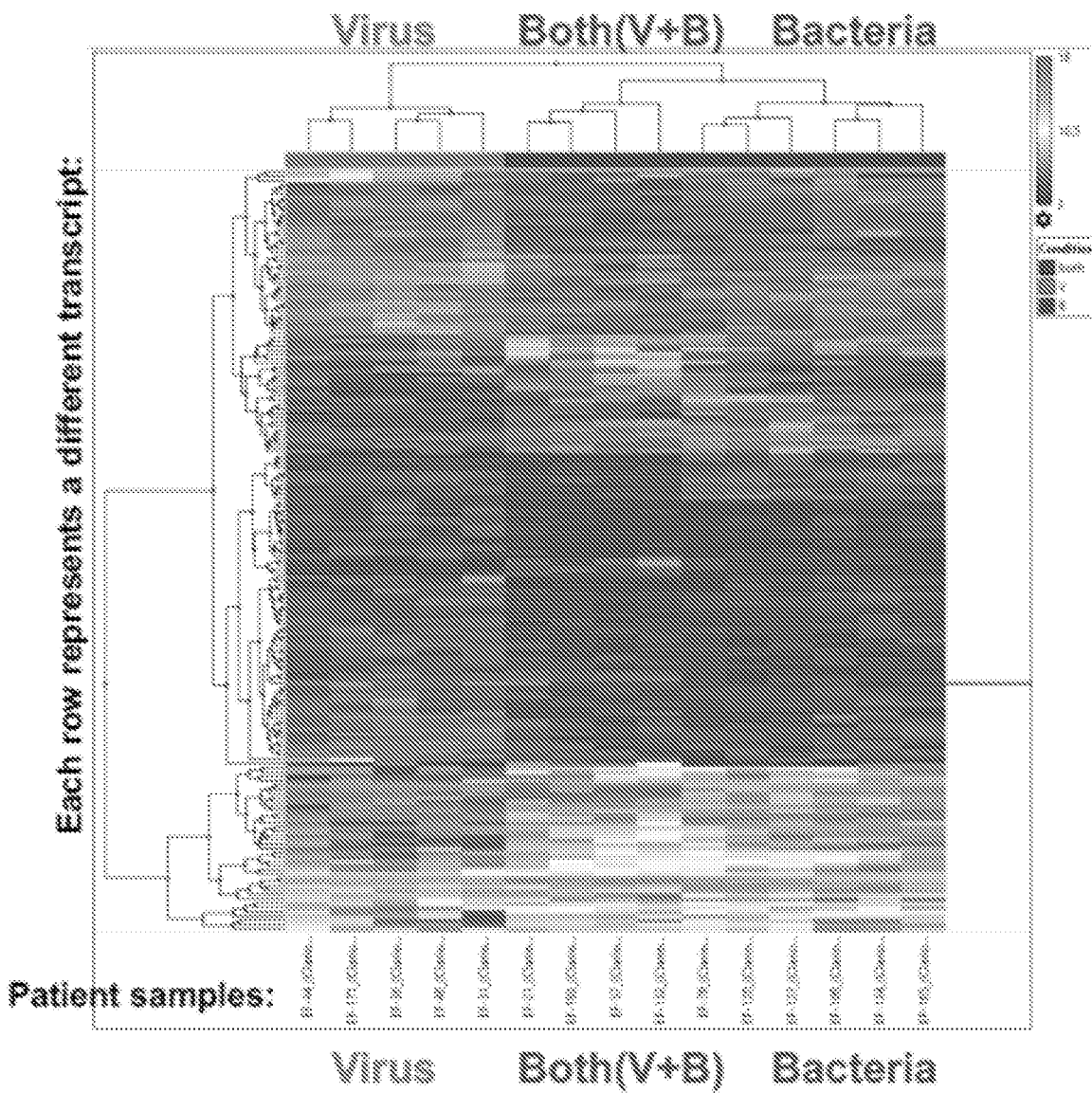
FIG. 1 depicts how transcriptome patterns in RNA isolated from patient throat swabs segregate viral-only pharyngitis from bacterial or viral+bacterial pharyngitis. Throat swabs were obtained from patients presenting with acute pharyngitis. Bacterial culture and testing for a panel of viral respiratory pathogens was performed on all samples to categorize the infection type as viral-only (red bar/font), bacterial-only (purple bar/font), or both (viral+bacterial, blue bar/font). RNA was isolated from samples and samples with sufficient RNA were sent for microarray analysis using Affymetrix pico-array chips. Using the Affymetrix software, hierarchical clustering was performed based on gene expression levels. The resulting dendrogram is shown, in which gene expression alone segregated viral-only infection from bacterial only or viral/bacterial co-infection.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "antimicrobial" or "antimicrobial agent" mean any compound with bacteriocidal or bacteriostatic activity which may be used for the treatment of bacterial infection. Non-limiting examples include antibiotics.

"Biological sample" or "sample" as used herein means a biological material isolated from an individual. The biological sample may contain any biological material suitable for detecting the desired biomarkers, and may comprise cellular and/or non-cellular material obtained from the individual. A biological sample may be of any biological tissue or fluid. Frequently the sample will be a "clinical sample" which is a sample derived from a patient. Typical clinical samples include, but are not limited to, bodily fluid samples such as synovial fluid, sputum, blood, urine, blood plasma, blood serum, sweat, mucous, saliva, lymph, bronchial aspirates, peritoneal fluid, cerebrospinal fluid, and pleural fluid, and tissues samples such as blood-cells (e.g., white cells), tissue or fine needle biopsy samples and abscesses or cells therefrom. Biological samples may also include sections of tissues, such as frozen sections or formalin fixed sections taken for histological purposes.

The terms "biomarker" or "marker," as used herein, refers to a molecule that can be detected. Therefore, a biomarker according to the present invention includes, but is not limited to, a nucleic acid, a polypeptide, a carbohydrate, a lipid, an inorganic molecule, an organic molecule, each of which may vary widely in size and properties. A "biomarker" can be a bodily substance relating to a bodily condition or disease. A "biomarker" can be detected using any means known in the art or by a previously unknown means that only becomes apparent upon consideration of the marker by the skilled artisan.

The term "biomarker (or marker) expression" as used herein, encompasses the transcription, translation, post-translation modification, and phenotypic manifestation of a gene, including all aspects of the transformation of information encoded in a gene into RNA or protein. By way of non-limiting example, marker expression includes transcription into messenger RNA (mRNA) and translation into protein. Measuring a biomarker also includes reverse transcription of RNA into cDNA (i.e. for reverse transcription-qPCR measurement of RNA levels).

As used herein, "biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as clinical parameters, as well as traditional laboratory risk factors. As defined by the Food and Drug Administration (FDA), a biomarker is a characteristic (e.g. measurable DNA and/or RNA) that is "objectively measured and evaluated as an indicator of normal biologic processes, pathogenic processes, or pharmacologic responses to a therapeutic intervention or other interventions". Biomarkers also include any calculated indices created mathematically or combinations of any one or more of the foregoing measurements, including temporal trends and differences.

As used herein, the term "carrier" means a subject having viral or bacterial respiratory pathogens, i.e. virus or bacteria, in their respiratory tract but in whom these pathogens are not currently causing disease. The carrier may or may not be contagious with respect to the respiratory pathogens carried.

The term "housekeeping gene" refers to a gene where it is practical to normalize the level of other genes against the level of expression of the housekeeping gene in order to control for variables such as, but not limited to, the total amount of biological material in the sample. β-actin is one possible example of a housekeeping gene.

By the phrase "determining the level of expression" is meant an assessment of the absolute or relative quantity of a biomarker in a sample at the nucleic acid or protein level, using technology available to the skilled artisan to detect a sufficient portion of any marker.

As used herein, an "immunoassay" refers to a biochemical test that measures the presence or concentration of a substance in a sample, such as a biological sample, using the reaction of an antibody to its cognate antigen, for example the specific binding of an antibody to a protein. Both the presence of the antigen or the amount of the antigen present can be measured.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The "level" of one or more biomarkers means the absolute or relative amount or concentration of the biomarker in the sample as determined by measuring mRNA, cDNA or protein, or any portion thereof such as oligonucleotide or peptide.

"Measuring" or "measurement," or alternatively "detecting" or "detection," means determining the presence, absence, quantity or amount (which can be an effective amount) of either a given substance within a clinical or subject-derived sample, including the derivation of qualitative or quantitative concentration levels of such substances, or otherwise determining the values or categorization of a subject's clinical parameters.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The terms "respiratory sample" or "respiratory swab sample" as used herein mean any sample from a subject containing RNA or secreted proteins a plurality of which is generated by cells in the respiratory tract. Non-limiting examples include nasal swabs, nasopharyngeal swabs, nasopharyngeal aspirate, oral swab, oropharyngeal swab, pharyngeal (throat) swab, sputum, bronchoalveolar lavage or saliva or transport medium exposed to any of these sample types.

The term "viral respiratory infection" as used herein means a virus that can cause or does cause a respiratory virus infection in a patient.

The term "bacterial respiratory infection" as used herein means a respiratory infection where the pathology is driven by bacteria.

The term "a bacterial-associated respiratory infection" refers to bacterial respiratory infections as well as bacterial and viral respiratory co-infections.

A "reference level" of a biomarker means a level of the biomarker that is indicative of the absence of a particular disease state or phenotype. When the level of a biomarker in a subject is above the reference level of the biomarker it is indicative of the presence of a particular disease state or phenotype. When the level of a biomarker in a subject is within the reference level of the biomarker it is indicative of a lack of a particular disease state or phenotype.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In one aspect the invention provides a method of detecting or distinguishing between a viral-only respiratory tract infection and a bacterial infection or viral/bacterial coinfection in a subject by detecting the patient's response to the infection. In various embodiments, the method comprises detecting a level of one or more respiratory infection-associated molecules produced by the body in the patient. The invention is based in part on the unexpected discovery that the host response to bacterial respiratory infection, as measured by determining a level of a bacterial respiratory infection associated molecule, masks the presence of a respiratory viral infection, as measured by determining a level of a viral respiratory associated molecule.

Respiratory Infection Type Associated Molecules

Messenger RNAs and proteins which change their level of expression in response to viral or bacterial infection are here called viral respiratory infection-associated or bacterial respiratory infection associated molecules. A viral respiratory infection-associated molecule may be any molecule the expression of which changes in a patient having a respiratory viral infection relative to a patient that does not have a respiratory viral infection, or relative to a patient that has a bacterial infection or vial/bacterial coinfection. This is illustrated in FIG. 1 for a variety of biomarkers.

Suitable genes were identified according to Example 1, and are shown in part in Table 1. By way of non-limiting example, viral respiratory infection-associated molecules may be identified by detecting them at a higher level in respiratory swabs from patients with viral-only infection compared to patients with bacterial infection or viral/bacterial co-infection (FIG. 1 and FIG. 2), or by stimulation of respiratory epithelial cells with a viral RNA mimetic such as SLR14 (column 4, FIGS. 2A and 2b). In various embodiments, the viral respiratory infection-associated molecule may be FAM160A1, CXCL9, CXCL11, IDO1, IRG1, TFEC, EPHA4, DGCR2, DGCR11, SAA2; SAA2-SAA4; SAA4, OR8B4, STAT2, ATP13A3, CXCL10, PLA2G7, DRAM1, ZNF407, MS4A7, ADGRD1, OR6C2, PTTG11P, NFAT5, GSN, EDA, ROBO2, PRNP, THRAP3, CCDC184, SEMA6D, SOCS6, ITPKC, DGKD, SRPRB, RNF148, TRIM67, CTH, ZMYND11, PNLIPRP3, MAP4, GAD2, KIDINS220, ST5, MCM3AP, LIPG, WBP5, ITPKA, WDR78, PNPT1, FAM184B, P2RX7, VAMP4, ARVCF, TEX9, OR52N4, TAAR2, CP, NIPSNAP3A, NIPSNAP3B, OSTM1, TRIM69, MDM1, SLC32A1, ERN2, LINC01521, AK4, EXOSC6, CHFR, FBXO43, HUS1B, PLCB1, CECR6 and DSG2. CXCL10 was evaluated as a biomarker differentiating viral-only infection from bacterial infection or viral/bacterial co-infection (FIG. 2). Accordingly, in various embodiments the viral-only respiratory infection-associated molecule may be CXCL10.

Figure 3A:
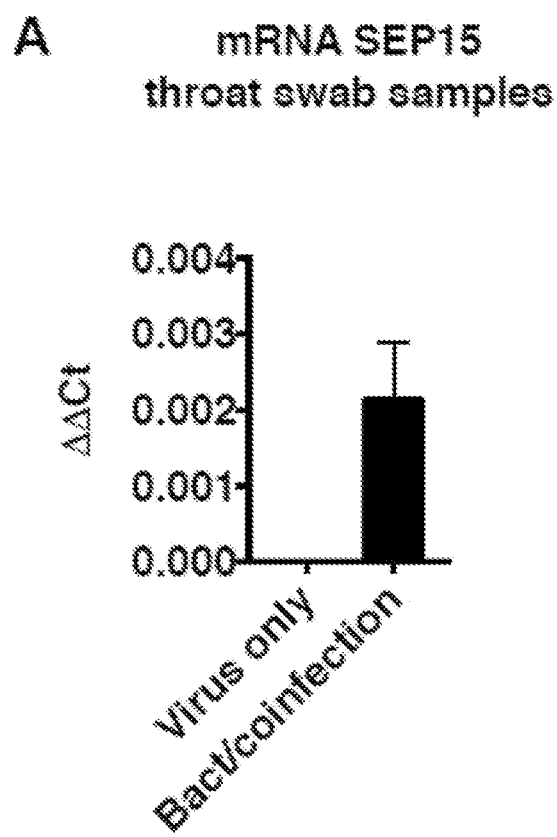
FIGS. 3A and 3B depict RT-qPCR validation of bacterial/coinfection biomarker SEP15.
Figure 3B:
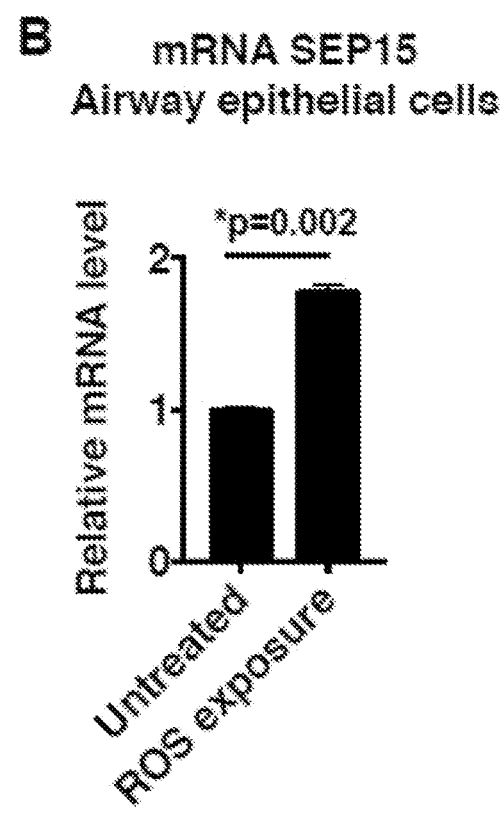

A bacterial respiratory infection-associated molecule may be any gene, the expression of is associated with a patient having a respiratory bacterial infection or viral/bacterial coinfection, relative to a patient that having a viral-only infection. By way of non-limiting examples, bacterial respiratory infection-associated molecules may be identified by detecting their response to hydrogen peroxide, other reactive oxygen species or other mimics of oxidative stress or ER stress associated with bacterial infection. Bacterial infection associated molecules may also include molecules expressed by inflammatory cells present in the respiratory tract in an activation state specific to bacterial infection, such as PROK2. In various embodiments, the bacterial respiratory infection-associated molecule may be SEP15, SLC25A40, ANKRD13A, H2AFZ, TLK1, ARPC2, BSG, MSRB1, PI3, SCAF8, TIAM2, ZMAT2, CAP1, ARPC3, LAMTOR5, ACAA1, RAP1A, SSR2, ZDHHC3, ZNF680, RHOG, PRKACB, SHOC2, CCDC126, FAM102A, TAF10, LSM1, NECAP1, PHB, SNX3, FAM122B, SEC63, U2AF1, ZC3H14, ARHGDIB, ATE1, PSMB7, FLI1, CRTC2, GHITM, UBE2D2, NFU1, IDH3A, ZNF791, PROK2, MLF2, MXI1, EIF4B, NUMA1, PCBD1, BAG6, STX7, CREB1, COPS3, C1orf43, FDFT1, VKORC1, ACTR10, CCND3, GOLGA7, TMEM167A, RPS8, SNORD55, SNORD46, SNORD38A, SNORD38B, ABTB1, HSD17B11, CAMK2G, ATG4C, PHF3, QRICH1, MTHFS, CDK5RAP2, UBE2W, DPY19L1, HIPK1, TXNIP, IRAK4, APOPT1 and TRMT112, PROK2. SEP15 was evaluated as a molecule to distinguish viral-only infection from bacterial or viral/bacterial coinfection and as a bacterial infection associated molecule inducible in airway epithelial cells by oxidative stress (FIG. 3).

Method for Detecting a Viral or a Bacterial Respiratory Infection in a Patient

In one aspect, the invention provides a method for detecting or distinguishing between viral-only infection in a patient from bacterial infection or viral/bacterial co-infection, by analyzing a respiratory swab sample to determine a level of at least one respiratory virus infection-associated molecule and/or a level of at least one bacterial respiratory infection-associated molecule and a level of a housekeeping gene by measuring mRNA. The level of the at least one respiratory virus infection-associated molecule and/or the level of the at least one bacterial respiratory infection-associated molecule are normalized to the level of the housekeeping gene to determine a normalized level of the at least one respiratory virus infection-associated molecule and/or a normalized level of the at least one bacterial respiratory infection-associated molecule. Comparing the normalized level of the at least one respiratory virus infection-associated molecule and/or the normalized level of the at least one bacterial respiratory infection-associated molecule with a predetermined reference level for the at least one respiratory virus infection-associated molecule and a predetermined reference level of the at least one bacterial respiratory infection-associated molecule indicates the respiratory infection status of the patient. If the normalized level of the at least one respiratory virus infection-associated molecule is above the respective reference level, the patient is determined to have a virus-only respiratory infection. If the normalized level of the at least one bacterial respiratory infection-associated molecule is above the respective reference level, the patient is determined to have a respiratory infection involving bacteria as at least a contributor to the host response (a bacterial associated respiratory infection).

In another aspect, the invention provides a method for detecting or distinguishing between a viral or a bacterial respiratory infection in a patient, by analyzing a respiratory sample to determine a level of at least one respiratory virus infection-associated molecule and a level of at least one bacterial respiratory infection-associated molecule by measuring protein. Comparing the level of the at least one respiratory virus infection-associated molecule and/or the level of the at least one bacterial respiratory infection-associated molecule with a predetermined reference level for the at least one respiratory virus infection-associated molecule and a predetermined reference level for the at least one bacterial respiratory infection-associated molecule indicates the respiratory infection status of the patient. If the level of the at least one respiratory virus infection-associated molecule is above the respective reference level, the patient is determined to have a viral-only respiratory infection. If the level of the at least one bacterial respiratory infection-associated molecule is above the respective reference level, the patient is determined to have a bacterial respiratory infection or coinfection.

In various embodiments the invention is directed to a method of distinguishing among infection types by collecting patient cells, cell debris, or cell free fluid from a respiratory swab sample. In some embodiments the respiratory swab samples are prepared by placing a respiratory sample in a media or solvent and releasing material from the respiratory sample into the media or solvent.

In various embodiments, the respiratory swab may be obtained from the nose, nasopharynx, mouth, oropharynx, throat or ears. Release of the material may be aided by stirring, vortexing or any other method known in the art or may simply occur by passive diffusion. Solvent may be of any type known in the art and may comprise various additives to stabilize viruses, bacteria, proteins or other biological materials including but not limited to pH buffers, antibiotics, and/or cryoprotectants such as sucrose.

While biomarkers distinguishing systemic viral and bacterial infection have been described using patient blood samples, unexpectedly, markers for host response are easily detectable in respiratory samples, by way of non-limiting example, by using swabs of the upper respiratory tract. Samples obtained by sampling the upper respiratory tract are much less invasive and are more directly relevant to disease pathogenesis than blood samples in the case of respiratory infection. Also, a surprising finding of our studies was that virus-only infection induces a different host response pattern than bacterial infection OR viral/bacterial coinfection, with coinfection clustering with bacterial-only infection in terms of host response pattern (FIG. 1). Various biomarkers may be detected in these samples as protein or as mRNA. Accordingly, in some embodiments expression of biomarkers is determined by measuring mRNA. In other embodiments, expression is determined by measuring protein.

In embodiments comprising the measurement of mRNA, the respiratory swab sample may be centrifuged to form a pellet of cells and cell debris which is then added to lysis buffer. Total nucleic acid is isolated from the pellet and DNA is digested using, by way of non-limiting example, DNAse I. The RNA is then reverse transcribed into cDNA. The cDNA is then analyzed to determine the level of at least one respiratory infection-associated molecule. In some embodiments the level of the at least one respiratory infection-associated molecule is determined by reverse transcription quantitative polymerase chain reaction (rt-qPCR) although the skilled artisan will appreciate that there are other ways that the level of the at least one respiratory infection-associated molecule may be determined by the analysis of mRNA and these methods are encompassed by the invention in its various embodiments. A skilled person is capable of selecting and practicing an appropriate technique as the measurement of levels of specific mRNAs and proteins in a sample is a familiar operation to a skilled artisan.

In embodiments comprising the measurement of protein, the respiratory swab sample may be used in an immunoassay. In various embodiments the proteins are secreted proteins, in some embodiments the proteins are chemokines.

In some embodiments, the expression level of the measured respiratory infection-associated molecules are normalized to the expression level of a housekeeping gene. The expression level of the housekeeping gene may be measured using the same method as the one or more respiratory infection-associated molecule. In some embodiments, the housekeeping gene is β-actin, HPRT, or GAPDH.

In another aspect, the invention provides a method of reducing the inappropriate use of antibiotics is also included. The method allows clinicians to distinguish between patients with bacterial respiratory infections or viral/bacterial coinfections for whom antibiotics may be beneficial and patients with viral respiratory infections who are not expected to benefit from treatment with antibiotics.

Some embodiments comprise a method of treating a patient exhibiting symptoms of respiratory infection comprising determining levels of respiratory infection-associated molecule by measuring either protein or mRNA. In various embodiments, patients exhibiting a level of the biomarker may be treated for respiratory viral infection or bacterial respiratory infection. In various embodiments, subjects determined to have a bacterial respiratory infection are treated with antibiotics. In various embodiments, subjects determined to have a viral respiratory infection are treated with antivirals or are treated by monitoring and recommending supportive care, such as rest and fluids. In other embodiments, the test result could be used as part of a diagnostic algorithm to guide further testing, such as which patients can be managed without further testing and which patients should receive additional testing, and which pathogen-specific tests are indicated. In another aspect, the invention provides a method of treating a patient by analyzing a respiratory sample to determine a level of at least one respiratory virus infection-associated molecule and/or a level of at least one bacterial respiratory infection-associated molecule by measuring mRNA or protein; comparing the level of the at least one bacterial respiratory infection-associated molecule with a predetermined reference level for the at least one bacterial respiratory infection-associated molecule; wherein if the level of the at least one bacterial respiratory infection-associated molecule is above the respective reference level, the patient is treated with antibiotics. In various embodiments, the antibiotic may be penicillin, amoxicillin or erythromycin.

In other embodiments, host response biomarkes described here could be used to differentiate incidental detection of microorgansism(s) in the upper respiratory tract from an active infectious process that the body is fighting. In recent years epidemiological surveys testing for a panel of respiratory viruses have repeatedly found high rates of respiratory virus detection even in the asymptomatic population. Similarly, strepotococcal bacteria which cause strep throat illnesses can also be present in the throat without causing symptoms ('carrier state".) This has raised questions about the usefulness of pathogen—specific tests, in particular sensitive PCR-based tests for pathogen genomes, to determine whether a detected mciroorganim is causing disease, or if several organisms are detected, which among those is causing disease. Clearly, the test can be positive in the absence of disease. In such cases, the host-response based tests described here may also be useful in differentiating a respiratory infection as the immediate cause of illness from incidental presence of viral and/or bacterial genomes in the upper respiratory tract, and distinguishing among various detected microbes as the likely cause of the patient's symptoms. The reference level may be set such that it indicates that a respiratory virus or bacterial infection is the cause for the patient's symptoms. Accordingly, in one aspect the invention provides a method of rule in in a specific type of active infectious process, which pathogen detection alone does not provide.

In various embodiments, the methods described herein may be used in combination with pathogen specific tests in order to, by way of non-limiting example, to determine the identity of the virus or bacteria that is responsible for the patient's symptoms and to guide treatment. In various embodiments, the pathogen specific tests may detect one or more of influenza A, influenza B, *Streptococcus*, coronavirus and respiratory syncytial virus. In various embodiments, pathogen specific tests for one or more virus may be performed subsequent to detection of a virus-only host response and pathogen specific tests for one or more bacteria may be performed subsequent to detection of a bacterial-associated host response.

In another aspect the invention provides a method of distinguishing whether a respiratory pathogen detected in a subject is part of an active disease process, or represents a non-pathogenic carrier state. For example, Group A *Streptococcus* can be present chronically in individuals in an asymptomatic carrier state or can be the proximal cause of an acute symptomatic illness. More information about whether detected Group A strep is part of the disease process would be useful in guiding treatment decisions. The presence of bacterial or viral respiratory pathogens in the respiratory tract of the subject may be determined by any means known in the art. If neither the level of at least one bacterial respiratory infection-associated molecule is below a reference level, the pathogen is determined to be unlikely to be part of the acute disease process.

In another aspect, the methods of the invention may be used to detect pre-symptomatic patients suffering from a viral or bacterial associated respiratory infection. Host response based expression changes of viral respiratory infection associated or bacterial respiratory infection may appear before the disease may be recognized based on the appearance of patient symptoms. Accordingly, the methods of the invention may be applied to individuals at risk of infection to predict the appearance of symptoms or to people in situations where the appearance of the symptoms of respiratory infection would cause unusually serious problems, by way of non-limiting example, prior to travel or undertaking work that would be compromised by a respiratory infection.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Using throat swabs from patients with viral infection, bacterial infection, or both, we found that the gene expression patterns in throat cells from patients with bacterial infection or viral/bacterial coinfection are similar, and distinct from gene expression patterns from patients with viral-only infection. Measurements of several individual biomarkers also recapitulated the information given by the whole transcriptome data (eg differentiated patients into viral-only vs bacterial or co-infection). See FIG. 1. CXCL10 was evaluated as a respiratory viral-infection associated molecule (FIG. 2) and SEP15 was evaluated a respiratory bacterial-infection associated molecule (FIG. 3). Table 1 below lists examples of respiratory infection associated molecules. In the table, negative fold change values indicate biomarkers associated with viral-only infection, and positive fold change values indicate enrichment in bacterial or viral/bacterial coinfection compared to virus-only infection.

TABLE 1

Virus-only vs. Bacterial/co-infection Biomarkers
(Log2FC > 2 or <-2, p < 0.01)

| Gene Symbol | Fold Change | P-val |
|---|---|---|
| Up in Viral-only | | |
| FAM160A1 | -10.14 | 0.007 |
| CXCL9 | -9.08 | 0.0004 |
| IDO1 | -5.24 | 0.0021 |
| IRG1 | -5.23 | 0.0029 |
| TFEC | -3.48 | 0.0015 |
| EPHA4 | -3.47 | 0.0015 |
| DGCR2; DGCR11 | -3.46 | 0.007 |
| SAA2; SAA2-SAA4; SAA4 | -3.39 | 0.0062 |
| OR8B4 | -3.32 | 0.0011 |
| STAT2 | -3.23 | 0.0091 |
| ATP13A3 | -3.18 | 0.0009 |
| CXCL10 | -3.16 | 0.0005 |
| PLA2G7 | -3.09 | 0.0068 |
| DRAM1 | -2.94 | 0.0031 |
| ZNF407 | -2.82 | 0.0026 |
| MS4A7 | -2.79 | 0.0056 |
| ADGRD1 | -2.68 | 0.0083 |
| OR6C2 | -2.64 | 0.0027 |
| PTTG1IP | -2.57 | 0.0076 |
| NFAT5 | -2.55 | 0.0007 |
| GSN | -2.51 | 0.0049 |
| EDA | -2.5 | 0.0001 |
| ROBO2 | -2.5 | 0.0053 |
| PRNP | -2.49 | 0.0022 |
| THRAP3 | -2.45 | 0.0004 |
| CCDC184 | -2.43 | 0.0004 |
| SEMA6D | -2.43 | 0.0053 |
| SOCS6 | -2.43 | 0.0009 |
| ITPKC | -2.38 | 0.0069 |
| DGKD | -2.36 | 0.0065 |
| SRPRB | -2.31 | 0.0058 |
| RNF148 | -2.3 | 0.0007 |
| TRIM67 | -2.29 | 0.0078 |
| CTH | -2.28 | 0.0088 |
| ZMYND11 | -2.25 | 0.0009 |
| PNLIPRP3 | -2.23 | 0.0004 |
| MAP4 | -2.22 | 0.0085 |
| GAD2 | -2.21 | 0.0017 |
| KIDINS220 | -2.21 | 0.0052 |
| ST5 | -2.21 | 0.0044 |

TABLE 1-continued

Virus-only vs. Bacterial/co-infection Biomarkers
(Log2FC > 2 or <-2, p < 0.01)

| Gene Symbol | Fold Change | P-val |
|---|---|---|
| MCM3AP | -2.2 | 0.0036 |
| LIPG | -2.19 | 0.0013 |
| WBP5 | -2.19 | 0.0018 |
| ITPKA | -2.18 | 0.0014 |
| WDR78 | -2.18 | 0.0067 |
| LFNG; MIR4648 | -2.17 | 0.0018 |
| PNPT1 | -2.17 | 0.0016 |
| FAM184B | -2.15 | 0.0077 |
| P2RX7 | -2.13 | 0.0006 |
| VAMP4 | -2.13 | 0.0012 |
| ARVCF | -2.12 | 0.0043 |
| TEX9 | -2.12 | 0.0013 |
| OR52N4 | -2.11 | 0.0015 |
| TAAR2 | -2.11 | 0.0011 |
| CP | -2.1 | 0.0042 |
| NIPSNAP3A; NIPSNAP3B | -2.1 | 0.004 |
| OSTM1 | -2.1 | 0.0023 |
| TRIM69 | -2.1 | 0.001 |
| MDM1 | -2.09 | 0.0013 |
| SLC32A1 | -2.09 | 0.007 |
| ERN2 | -2.08 | 0.0004 |
| LINC01521 | -2.07 | 0.0091 |
| AK4 | -2.06 | 0.0004 |
| EXOSC6 | -2.05 | 0.0012 |
| CHFR | -2.04 | 0.0067 |
| FBXO43 | -2.04 | 0.0014 |
| HUS1B | -2.04 | 0.0025 |
| PLCB1 | -2.04 | 0.0031 |
| CECR6 | -2.02 | 0.007 |
| DSG2 | -2.01 | 0.0087 |
| ANO1 | -2 | 0.007 |
| Up in Bacterial or Co-infection | | |
| SEP15 | 7.85 | 5.26E-05 |
| SLC25A40 | 2.87 | 7.97E-05 |
| ANKRD13A | 10.19 | 0.0002 |
| H2AFZ | 5.89 | 0.0002 |
| TLK1 | 2.25 | 0.0004 |
| ARPC2 | 7 | 0.0005 |
| BSG | 3.95 | 0.0008 |
| MSRB1 | 16.34 | 0.001 |
| PI3 | 19.48 | 0.001 |
| SCAF8; TIAM2 | 2.07 | 0.001 |
| ZMAT2 | 3.17 | 0.001 |
| CAP1 | 3.82 | 0.0012 |
| ARPC3 | 5.6 | 0.0017 |
| LAMTOR5 | 14.26 | 0.0017 |
| ACAA1 | 3.61 | 0.0018 |
| RAP1A | 3.71 | 0.0018 |
| SSR2 | 10.85 | 0.0018 |
| ZDHHC3 | 3.78 | 0.0018 |
| ZNF680 | 3 | 0.002 |
| RHOG | 3.33 | 0.0022 |
| PRKACB | 5.49 | 0.0023 |
| SHOC2 | 2.07 | 0.0026 |
| CCDC126 | 6.22 | 0.0027 |
| FAM102A | 3.54 | 0.0028 |
| TAF10 | 2.47 | 0.0028 |
| LSM1 | 2.31 | 0.0029 |
| NECAP1 | 2.26 | 0.0034 |
| PHB | 3.23 | 0.0036 |
| SNX3 | 2.1 | 0.0037 |
| FAM122B | 2.39 | 0.0038 |
| SEC63 | 3.77 | 0.0038 |
| U2AF1 | 2.57 | 0.0038 |
| ZC3H14 | 2.3 | 0.0038 |
| ARHGDIB | 6.64 | 0.0039 |
| ATE1 | 2.27 | 0.0039 |
| PSMB7 | 2.11 | 0.0039 |
| FLI1 | 3.15 | 0.004 |
| CRTC2 | 2.16 | 0.0043 |
| GHITM | 2.36 | 0.0043 |
| UBE2D2 | 7.57 | 0.0043 |
| NFU1 | 2.74 | 0.0047 |
| IDH3A | 11.12 | 0.0049 |

TABLE 1-continued

Virus-only vs. Bacterial/co-infection Biomarkers
(Log2FC > 2 or <-2, p < 0.01)

| Gene Symbol | Fold Change | P-val |
|---|---|---|
| ZNF791 | 2.24 | 0.005 |
| PROK2 | 99.46 | 0.0051 |
| MLF2 | 2.14 | 0.0054 |
| MXI1 | 2.28 | 0.0054 |
| EIF4B | 4.69 | 0.0055 |
| NUMA1 | 2.01 | 0.0057 |
| PCBD1 | 2.13 | 0.0057 |
| BAG6 | 2.7 | 0.0059 |
| STX7 | 2.16 | 0.0059 |
| CREB1 | 2.29 | 0.0061 |
| COPS3 | 6.8 | 0.0062 |
| C1orf43 | 3.78 | 0.0066 |
| FDFT1 | 2.89 | 0.0066 |
| VKORC1 | 5.28 | 0.0066 |
| ACTR10 | 2.67 | 0.0067 |
| CCND3 | 3.41 | 0.0068 |
| GOLGA7 | 2.75 | 0.0069 |
| TMEM167A | 3.58 | 0.0069 |
| RPS8; SNORD55; SNORD46; SNORD38A; SNORD38B | 3.91 | 0.0071 |
| ABTB1 | 2.6 | 0.0072 |
| HSD17B11 | 3.64 | 0.0076 |
| CAMK2G | 2.14 | 0.0077 |
| ATG4C | 2.92 | 0.0078 |
| PHF3 | 3.14 | 0.0078 |
| QRICH1 | 2.83 | 0.0082 |
| MTHFS | 4.24 | 0.0083 |
| CDK5RAP2 | 2.61 | 0.0084 |
| UBE2W | 2.17 | 0.0084 |
| DPY19L1 | 5.34 | 0.0091 |
| HIPK1 | 2.35 | 0.0092 |
| TXNIP | 6.43 | 0.0097 |
| IRAK4 | 2.65 | 0.0098 |
| APOPT1 | 2.04 | 0.0099 |
| TRMT112 | 5.84 | 0.0099 | bold = experimental confirmation with Rt-qPCR

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for detecting a viral-only or a bacterial-associated respiratory infection in a patient, the method comprising:
   a. analyzing a respiratory sample from the patient to determine a level of at least one respiratory virus infection-associated molecule and a level of at least one bacterial respiratory infection-associated molecule and a level of a housekeeping gene by measuring mRNA, wherein the at least one respiratory virus infection-associated molecule comprises FAM160A1 and the at least one bacterial respiratory infection-associated molecule comprises SEP15;
   b. normalizing the level of the at least one respiratory virus infection-associated molecule and the level of the at least one bacterial respiratory infection-associated molecule to the level of the housekeeping gene to determine a normalized level of the at least one respiratory virus infection-associated molecule and a normalized level of the at least one bacterial respiratory infection-associated molecule; and
   c. comparing the normalized level of the at least one respiratory virus infection-associated molecule and the normalized level of the at least one bacterial respiratory infection-associated molecule with a predetermined reference level for the at least one respiratory virus infection-associated molecule and a predetermined reference level of the at least one bacterial respiratory infection-associated molecule, respectively;
   wherein if the normalized level of the at least one respiratory virus infection-associated molecule is above the respective reference level, the patient is determined to have a respiratory viral infection; and
   if the normalized level of the at least one bacterial respiratory infection-associated molecule is above the respective reference level, the patient is determined to have a bacterial-associated respiratory infection.

2. The method of claim 1, wherein the mRNA is measured by reverse transcription-qPCR.

3. The method of claim 1, wherein the at least one respiratory virus infection-associated molecule further comprises one or more respiratory virus infection-associated molecules selected from the group consisting of CXCL9, CXCL11, IDO1, IRG1, TFEC, EPHA4, DGCR2, DGCR11, SAA2; SAA2-SAA4; SAA4, OR8B4, STAT2, ATP13A3, CXCL10, PLA2G7, DRAM1, ZNF407, MS4A7, ADGRD1, OR6C2, PTTG1IP, NFAT5, GSN, EDA, ROBO2, PRNP, THRAP3, CCDC184, SEMA6D, SOCS6, ITPKC, DGKD, SRPRB, RNF148, TRIM67, CTH, ZMYND11, PNLIPRP3, MAP4, GAD2, KIDINS220, ST5, MCM3AP, LIPG, WBP5, ITPKA, WDR78, PNPT1, FAM184B, P2RX7, VAMP4, ARVCF, TEX9, OR52N4, TAAR2, CP, NIPSNAP3A, NIPSNAP3B, OSTM1, TRIM69, MDM1, SLC32A1, ERN2, LINC01521, AK4, EXOSC6, CHFR, FBXO43, HUS1B, PLCB1, CECR6 and DSG2.

4. The method of claim 3, wherein the at least one respiratory virus infection-associated molecule further comprises CXCL10.

5. The method of claim 1, wherein the at least one bacterial respiratory infection-associated molecule further comprises one or more bacterial respiratory infection-associated molecules selected from the group consisting of SLC25A40, ANKRD13A, H2AFZ, TLK1, ARPC2, BSG, MSRB1, PI3, SCAF8, TIAM2, ZMAT2, CAP1, ARPC3, LAMTOR5, ACAA1, RAP1A, SSR2, ZDHHC3, ZNF680, RHOG, PRKACB, SHOC2, CCDC126, FAM102A, TAF10, LSM1, NECAP1, PHB, SNX3, FAM122B, SEC63, U2AF1, ZC3H14, ARHGDIB, ATE1, PSMB7, FLI1, CRTC2, GHITM, UBE2D2, NFU1, IDH3A, ZNF791, PROK2, MLF2, MXI1, EIF4B, NUMA1, PCBD1, BAG6, STX7, CREB1, COPS3, C1orf43, FDFT1, VKORC1, ACTR10, CCND3, GOLGA7, TMEM167A, RPS8, SNORD55, SNORD46, SNORD38A, SNORD38B, ABTB1, HSD17B11, CAMK2G, ATG4C, PHF3, QRICH1, MTHFS, CDK5RAP2, UBE2W, DPY19L1, HIPK1, TXNIP, IRAK4, APOPT1, PROK2 and TRMT112.

6. The method of claim 1, wherein the housekeeping gene comprises β-actin, HPRT, or GAPDH.

7. A method for detecting a viral-only or a bacterial-associated respiratory infection in a patient, the method comprising:
   a. analyzing a respiratory sample from the patient to determine a level of at least one respiratory virus infection-associated molecule and a level of at least one bacterial respiratory infection-associated molecule by measuring protein, wherein the at least one respiratory virus infection-associated molecule comprises FAM160A1 and the at least one bacterial respiratory infection-associated molecule comprises SEP15; and b. comparing the level of the at least one respiratory virus infection-associated molecule and the level of the at least one bacterial respiratory infection-associated molecule with a predetermined reference level for the at least one respiratory virus infection-associated molecule and a predetermined reference level of the at least one bacterial respiratory infection-associated molecule, respectively;

wherein if the level of the at least one respiratory virus infection-associated molecule is above the respective reference level, the patient is determined to have a respiratory viral infection; and if the level of the at least one bacterial respiratory infection-associated molecule is above the respective reference level, the patient is determined to have a bacterial-associated respiratory infection.

8. The method of claim 7, wherein the level of the at least one respiratory virus infection-associated molecule and the level of the at least one bacterial respiratory infection-associated molecule is measured by immunoassay.

9. The method of claim 8, wherein the at least one respiratory virus infection-associated molecule comprises one or more respiratory virus infection-associated molecules selected from the group consisting of CXCL9, IDO1, IRG1, TFEC, EPHA4, DGCR2, DGCR11, SAA2; SAA2-SAA4; SAA4, OR8B4, STAT2, ATP13A3, CXCL10, PLA2G7, DRAM1, ZNF407, MS4A7, ADGRD1, OR6C2, PTTG1IP, NFAT5, GSN, EDA, ROBO2, PRNP, THRAP3, CCDC184, SEMA6D, SOCS6, ITPKC, DGKD, SRPRB, RNF148, TRIM67, CTH, ZMYND11, PNLIPRP3, MAP4, GAD2, KIDINS220, ST5, MCM3AP, LIPG, WBP5, ITPKA, WDR78, PNPT1, FAM184B, P2RX7, VAMP4, ARVCF, TEX9, OR52N4, TAAR2, CP, NIPSNAP3A, NIPSNAP3B, OSTM1, TRIM69, MDM1, SLC32A1, ERN2, LINC01521, AK4, EXOSC6, CHFR, FBXO43, HUS1B, PLCB1, CECR6 and DSG2.

10. The method of claim 9, wherein the at least one respiratory virus infection-associated molecule further comprises CXCL10.

11. The method of claim 7, wherein the at least one bacterial respiratory infection-associated molecule further comprises one or more bacterial respiratory infection-associated molecules selected from the group consisting of SLC25A40, ANKRD13A, H2AFZ, TLK1, ARPC2, BSG, MSRB1, PI3, SCAF8, TIAM2, ZMAT2, CAP1, ARPC3, LAMTOR5, ACAA1, RAP1A, SSR2, ZDHHC3, ZNF680, RHOG, PRKACB, SHOC2, CCDC126, FAM102A, TAF10, LSM1, NECAP1, PHB, SNX3, FAM122B, SEC63, U2AF1, ZC3H14, ARHGDIB, ATE1, PSMB7, FLI1, CRTC2, GHITM, UBE2D2, NFU1, IDH3A, ZNF791, PROK2, MLF2, MXI1, EIF4B, NUMA1, PCBD1, BAG6, STX7, CREB1, COPS3, C1orf43, FDFT1, VKORC1, ACTR10, CCND3, GOLGA7, TMEM167A, RPS8, SNORD55, SNORD46, SNORD38A, SNORD38B, ABTB1, HSD17B11, CAMK2G, ATG4C, PHF3, QRICH1, MTHFS, CDK5RAP2, UBE2W, DPY19L1, HIPK1, TXNIP, IRAK4, APOPT1, PROK2 and TRMT112.

12. The method of claim 1, wherein the levels of at least two respiratory virus infection-associated molecules and/or at least two bacterial respiratory infection-associated molecules are determined and compared to the respective reference.

13. The method of claim 1, wherein the levels of at least three respiratory virus infection-associated molecules and/or at least three bacterial respiratory infection-associated molecules are determined and compared to the respective reference levels.

14. A method of treating a patient exhibiting symptoms of a respiratory infection, the method comprising:

a. analyzing a respiratory sample from the patient to determine a level of at least one respiratory virus infection-associated molecule and a level of at least one bacterial respiratory infection-associated molecule and a level of a housekeeping gene by measuring mRNA, wherein the at least one respiratory virus infection-associated molecule comprises FAM160A1 and the at least one bacterial respiratory infection-associated molecule comprises SEP15;

b. normalizing the level of the at least one respiratory virus infection-associated molecule and the level of the at least one bacterial respiratory infection-associated molecule to the level of the housekeeping gene to determine a normalized level of the at least one respiratory virus infection-associated molecule and a normalized level of the at least one bacterial respiratory infection-associated molecule; and c. comparing the normalized level of the at least one respiratory virus infection-associated molecule and the normalized level of the at least one bacterial respiratory infection-associated molecule with a predetermined reference level for the at least one respiratory virus infection-associated molecule and a predetermined reference level of the at least one bacterial respiratory infection-associated molecule, respectively;

wherein if the normalized level of the at least one respiratory virus infection-associated molecule is above the respective reference level, the patient is treated for a respiratory viral infection; and if the normalized level of the at least one bacterial-associated molecule is above the respective reference level, the patient is treated for a bacterial respiratory infection.

15. A method of treating a patient exhibiting symptoms of a respiratory infection, the method comprising:

a. analyzing a respiratory sample from the patient to determine a level of at least one respiratory virus infection-associated molecule and a level of at least one bacterial respiratory infection-associated molecule by measuring protein, wherein the at least one respiratory virus infection-associated molecule comprises FAM160A1 and the at least one bacterial respiratory infection-associated molecule comprises SEP15; and b. comparing the level of the at least one respiratory virus infection-associated molecule and the level of the at least one bacterial respiratory infection-associated molecule with a predetermined reference level for the at least one respiratory virus infection-associated molecule and a predetermined reference level of the at least one bacterial respiratory infection-associated molecule, respectively;

wherein if the normalized level of the at least one respiratory virus infection-associated molecule is above the respective reference level, the patient is treated for a respiratory viral infection; and if the normalized level of the at least one bacterial-associated molecule is above the respective reference level, the patient is treated for a bacterial respiratory infection.

16. A method of determining whether a subject who tests positive for the presence of a bacterial or viral respiratory pathogen is a carrier or if the pathogen is part of a disease process, the method comprising:
 a. analyzing a respiratory sample from the subject to determine a level of at least one respiratory virus infection-associated molecule, a level of at least one bacterial respiratory infection-associated molecule, and a level of a housekeeping gene by measuring mRNA, wherein the at least one respiratory virus infection-associated molecule comprises FAM160A1 and the at least one bacterial respiratory infection-associated molecule comprises SEP15;
 b. normalizing the level of the at least one respiratory virus infection-associated molecule and the level of the at least one bacterial respiratory infection-associated molecule to the level of the housekeeping gene to determine a normalized level of the at least one respiratory virus infection-associated molecule and a normalized level of the at least one bacterial respiratory infection-associated molecule; and
 c. comparing the normalized level of the at least one respiratory virus infection-associated molecule and the normalized level of the at least one bacterial respiratory infection-associated molecule with a predetermined reference level for the at least one respiratory virus infection-associated molecule and a predetermined reference level of the at least one bacterial respiratory infection-associated molecule, respectively;
  wherein if the normalized level of the at least one respiratory virus infection-associated molecule is above the respective reference level, the subject is determined to have a respiratory viral infection;
  if the normalized level of the at least one bacterial respiratory infection-associated molecule is above the respective reference level, the subject is determined to have a bacterial-associated respiratory infection;
  if the normalized level of the at least one respiratory virus infection-associated molecule is above the respective reference level and the level of the at least one bacterial respiratory infection-associated molecule is above the respective reference level, the subject is determined to have both a respiratory viral infection and a bacterial respiratory infection; and
  if neither the level of the at least one respiratory virus infection-associated molecule nor the level of the at least one bacterial respiratory infection-associated molecule is above the respective reference level, the subject is determined to be a carrier.

17. A method of determining whether a subject who tests positive for the presence of a bacterial or viral respiratory pathogen is a carrier or if the pathogen is part of a disease process, the method comprising:
 a. analyzing a respiratory sample from the subject to determine a level of at least one respiratory virus infection-associated molecule and a level of at least one bacterial respiratory infection-associated molecule by measuring protein, wherein the at least one respiratory virus infection-associated molecule comprises FAM160A1 and the at least one bacterial respiratory infection-associated molecule comprises SEP15; and
 b. comparing the level of the at least one respiratory virus infection-associated molecule and the level of the at least one bacterial respiratory infection-associated molecule with a predetermined reference level for the at least one respiratory virus infection-associated molecule and a predetermined reference level of the at least one bacterial respiratory infection-associated molecule, respectively;
  wherein if the level of the at least one respiratory virus infection-associated molecule is above the respective reference level, the subject is determined to have a respiratory viral infection;
  if the level of the at least one bacterial respiratory infection-associated molecule is above the respective reference level, the subject is determined to have a bacterial respiratory infection;
  if the level of the at least one respiratory virus infection-associated molecule is above the respective reference level and the level of the at least one bacterial respiratory infection-associated molecule is above the respective reference level, the subject is determined to have both a respiratory viral infection and a bacterial respiratory infection; and
  if neither the level of the at least one respiratory virus infection-associated molecule nor the level of the at least one bacterial respiratory infection-associated molecule is above the respective reference level, the subject is determined to be a carrier.

18. A method of detecting a bacterial-associated respiratory infection in a subject, the method comprising:
 a. analyzing a respiratory sample from the subject to determine a level of at least one bacterial respiratory infection-associated molecule and a level of a housekeeping gene by measuring mRNA, wherein the at least one bacterial respiratory infection-associated molecule comprises SEP15;
 b. normalizing the level of the at least one bacterial respiratory infection-associated molecule to the level of the housekeeping gene to determine a normalized level of the at least one bacterial respiratory infection-associated molecule; and
 c. comparing the normalized level of the at least one bacterial respiratory infection-associated molecule with a predetermined reference level of the at least one bacterial respiratory infection-associated molecule;
  wherein if the normalized level of the at least one bacterial respiratory infection-associated molecule is above the respective reference level, the subject is determined to have a bacterial-associated respiratory infection.

19. A method of detecting a bacterial-associated respiratory infection in a subject, the method comprising:
 a. analyzing a respiratory sample from the subject to determine a level of at least one bacterial respiratory infection-associated molecule by measuring protein, wherein the at least one bacterial respiratory infection-associated molecule comprises SEP15; and
 b. comparing the level of the at least one bacterial respiratory infection-associated molecule with a predetermined reference level for the at least one bacterial respiratory infection-associated molecule;
  wherein if the level of the at least one bacterial respiratory infection-associated molecule is above the respective reference level, the subject is determined to have a bacterial respiratory infection.

20. The method of claim 18, wherein the housekeeping gene comprises β-actin, HPRT, or GAPDH.

* * * * *